United States Patent [19]

Sadun et al.

[11] Patent Number: 5,763,446

[45] Date of Patent: Jun. 9, 1998

[54] USE OF PENTOXIFYLLINE AND OTHER TUMOR NECROSIS FACTOR BLOCKERS FOR THE TREATMENT OF AIDS-ASSOCIATED OPTIC NEUROPATHY AND OTHER CENTRAL NERVOUS SYSTEM DISEASES

[75] Inventors: Alfredo A. Sadun, San Marino; Parkash S. Gill, Agoura Hills; Pravin U. Dugel, Alhambra, all of Calif.; Michele Madigan, Hurlstone Park, Australia

[73] Assignee: University of Southern California, Los Angeles, Calif.

[21] Appl. No.: 858,129

[22] Filed: Mar. 26, 1992

[51] Int. Cl.$^6$ ............................. A61K 31/52; C07K 1/00
[52] U.S. Cl. ............................................ 514/263; 530/351
[58] Field of Search ............................ 530/351; 514/263

[56] References Cited

U.S. PATENT DOCUMENTS 5,096,906  3/1992  Mandell et al. ........................ 514/263

FOREIGN PATENT DOCUMENTS 9115451  10/1971  WIPO .

OTHER PUBLICATIONS

Sullivan et al., Inhibition of the Inflammatory Action of Interleukin–1 and Tumor Necrosis Factor (Alpha) on Neutrophil Function by Pentoxifylline, Infection and Immunity, vol. 56:1722–1729 (1988).

Strieter et al., Cellular and Molecular Regulation of Tumor Necrosis Factor Alpha Production by Pentoxifylline, Biochemical and Biophysical Research Communication vol. 155:1230–1236 (1988).

Schade, Ulrich F., Pentoxifylline Increases Survival in Murine Endotoxin Shock and Decreases Formation of Tumor Necrosis Factor, Circulatory Shock vol. 31:171–181 (1990).

Novick et al., New Pharmacological Studies with Pentoxifylline, Biorheology vol. 27:449–454 (1990).

Noel et al., Pentoxifylline Inhibits Lipopolysaccharide–induced Serum Tumor Necrosis Factor and Mortality, Life Sciences vol. 47:1023–1029 (1990).

Biosis Abstract of Pharmatherapeutica, vol. 2, Jul. 1980, pp. 429–438, "Clinical Use of Pentoxifylline in Hemorrhagic Disorders of the Retina".

Kopmels et al., J. Neuroimmunol. (Suppl. 1) 1991 p. 148.

Strieter et al., Biochem. Biophys. Res. Commun., vol. 155, No. 3, 1988, pp. 1230–1236.

Fazely et al., "Pentoxifylline (Trental) Decreases the Replication of the Human Immunodeficiency Virus Type 1 in Human Peripheral . . . ." Blood, 77, pp. 1653 (1991).

Dugel et al., "Tumor Necrosis Factor in AIDS Associated Optic Neuropathy," Invest. Ophthalmol. Visual Sci., 32, (4) 1991, p. 765.

Busse et al, "Neuritis nervi optici—results of an etiological inquiry & therapeutical results." Medline Abstract #80030891, Klin Monatsbl Augenheilkd, 175, 1979.

Primary Examiner—Deborah Lambkin
Attorney, Agent, or Firm—Pretty, Schroeder & Poplawski

[57] ABSTRACT

In accordance with the present invention, methods are provided for the treatment of visual loss and other neurological dysfunctions in AIDS patients employing agents capable of blocking TNF expression in the central nervous system.

18 Claims, 1 Drawing Sheet

USE OF PENTOXIFYLLINE AND OTHER TUMOR NECROSIS FACTOR BLOCKERS FOR THE TREATMENT OF AIDS-ASSOCIATED OPTIC NEUROPATHY AND OTHER CENTRAL NERVOUS SYSTEM DISEASES

ACKNOWLEDGEMENT

This invention was made partly with Government support under grant number EY08145, awarded by the National Institutes of Health. The Government has certain rights in the invention.

FIELD OF THE INVENTION

The present invention relates to treatment of central nervous system (CNS) diseases that manifest as white matter degeneration. In a particular aspect, the invention relates to the treatment of optic neuropathy and other CNS impairments associated with acquired immunodeficiency syndrome (AIDS). In another aspect, the invention relates to treatment of optic neuropathy and other CNS impairments due to immune disorder diseases such as multiple sclerosis.

BACKGROUND OF THE INVENTION

Acquired immunodeficiency syndrome (AIDS) patients frequently present with a variety of clinical symptoms associated with peripheral and central nervous system (CNS) disorders. Clinical investigations have found neurological disorders in about 40–60% of adult AIDS patients, while postmortem studies have found neuropathological changes in 70–80% of AIDS patients. Initially, neurological changes were thought to be secondary to AIDS-related conditions such as opportunistic infections [e.g., toxoplasmosis, cryptococcal meningitis and viral infections, particularly cytomegalovirus (CMV)]; cerebral lesions, and neoplasms. However, it has since become clear that primary human immunodeficiency virus (HIV) infection of the CNS is probably directly responsible for the AIDS dementia or encephalopathy increasingly noted in AIDS patients.

In some cases, neurological disorders may be the only presenting manifestation of HIV infection. Pathological features of the AIDS-infected CNS include progressive diffuse leukoencephalopathy (PDL), diffuse myelination, focal cerebral atrophy, astroglial proliferation, lymphocyte infiltration, microglial nodules, perivascular inflammation, and multinucleated giant cells (MGCs). White matter pallor seems to be due to myelin degeneration and cellular infiltrates; axonal loss may also occur as myelin destruction progresses. HIV and HIV-specific antibodies have been identified in the CNS and cerebrospinal fluid (CSF) of AIDS patients using immunocytochemistry, in situ hybridization, direct viral isolation, immunoblot assays and electron microscopy. There is little evidence for direct HIV-infection of neurons in the CNS, although some studies indicate that astrocytes and endothelial cells may contain the virus. The virus has been found mainly in mononuclear phagocyte series (MPS) cells and microglia, which can transmit HIV across the blood-brain barrier to the CNS and CSF.

Ophthalmological studies of AIDS patients have also found a difference between the incidence of presentation of clinical ocular signs (40–70% of patients), and of postmortem ocular lesions (up to 90% of patients). Common ocular findings include CMV retinitis, cotton wool spots (nerve fiber layer infarcts), conjunctival Kaposi's sarcoma, progressive or acute retinal necrosis, optic neuropathies and neuro-ophthalmic disorders. Visual field defects have been reported in AIDS patients, some with secondary infections. Additionally, visual impairment has recently been demonstrated in AIDS patients without retinitis (and best corrected distance Snellen visual acuity if 20/20 or better), consistent with dysfunction of the optic nerve [see Quiceno et al., in American Journal of Ophthalmology 113:8–13 (1992)]. A significant decrease in normal color discrimination and contrast threshold deficits in four of five spatial frequencies were found in closely followed AIDS patients without any form of retinitis [see Quiceno et al., supra]. Pathological examination of optic nerves in similar retinitis-free AIDS patients disclosed both axonal degeneration and gliosis suggestive of a primary AIDS-related optic neuropathy [see Tenhula et al., in American Journal of Ophthalmology 113:14–20 (1992)].

Using the paraphenylenediamine (PPD) technique described by Sadun and Schaechter in J. Electron Microsc. Tech. 2:175–186 (1985), axonal degeneration and a significant decrease in the number of intact axons was found in AIDS patients without apparent retinitis or obvious ophthalmological findings.

Cross sectional observational studies have also shown that retinal fiber layer infarcts occur in nearly all AIDS patients and that the number of infarcts increase over time. Therefore, the visual deficit reported in AIDS patients without retinitis may in part be related to the cumulative effects of anterograde degeneration secondary to retinal nerve fiber layer infarcts. However, it is more likely that most of the visual dysfunction and the optic nerve degeneration observed in AIDS patients is due to a primary optic neuropathy. The diffuse nature of AIDS optic nerve degeneration shows normal axons adjacent to degenerated axons, unlike the focal clusters of degenerated axons expected with retinal nerve fiber layer infarcts or other discrete retinal lesions. Moreover, clinical studies demonstrate the occurrence of mid-spatial frequency losses not characteristic of retinal disease with 20/20 to 20/30 vision. In the absence of secondary opportunistic infections, axonal degeneration may be produced by direct viral infection of the axons. Alternatively, direct destruction of myelin by activated MPS cells may occur. HIV may also indirectly mediate axonal degeneration via humoral factors (e.g., immunoglobulins and the activation of the complement cascade) and/or cellular factors released from HIV-infected cells that may directly damage axons or adversely influence adjacent glia.

It would be desirable, therefore, to identify the cause(s) of visual dysfunction and destruction of myelin in AIDS patients, so that effective treatments for such disease states can be developed.

BRIEF DESCRIPTION OF THE INVENTION

In accordance with the present invention, it has been discovered that there is a correlation between neurological dysfunction in AIDS patients and elevated CSF TNF levels. Accordingly, methods are provided for the treatment of such disease states employing agents capable of blocking TNF expression or neutralizing TNF present in the central nervous system.

The specific applications of TNF blockers described herein represent new applications for such compounds, as the prior art has previously considered the presence of substantial quantities of TNF to be beneficial with respect to the disease states which are contemplated for treatment according to the present invention.

DETAILED DESCRIPTION OF THE INVENTION

Figure 1:
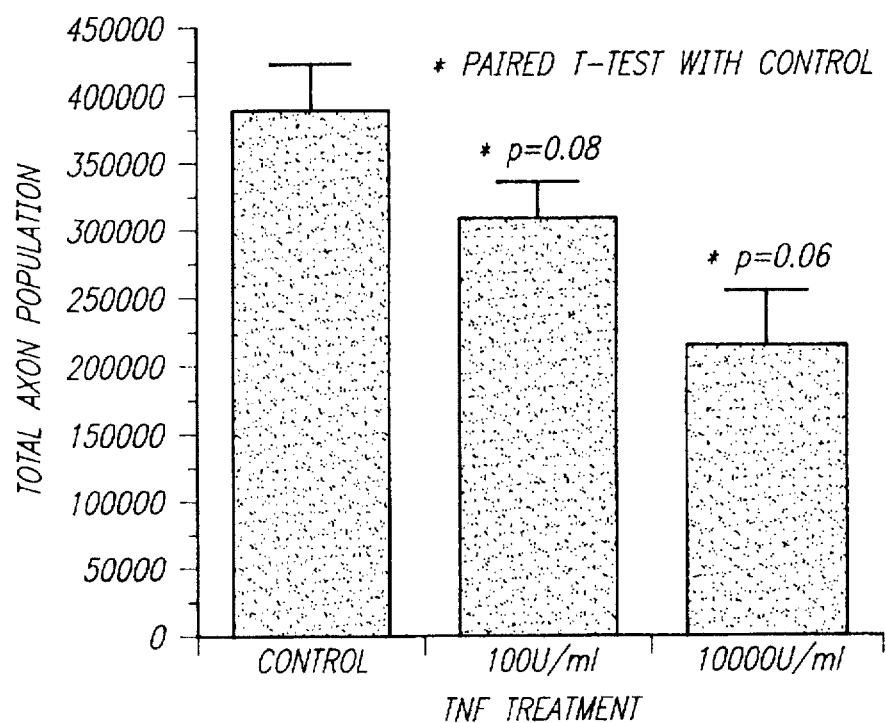
FIG. 1 shows the effect of TNF treatment on rabbit optic nerve axon population as a function of dosage.

Ultrastructural studies of the AIDS optic nerve reveal activated astrocytes and MPS cells, and the oligodendrocyte pathology associated with axonal degeneration, suggesting that AIDS optic neuropathy occurs at the level of the nerve itself, rather than via retinal changes. Similar observations have been made in the CNS of HIV-infected patients with other neurological disorders. These observations suggest that CNS changes seen in AIDS patients are more likely due to the indirect effects of local factors such as cytokines on the CNS. While it is possible that these changes may be due to remote effects of axonal damage elsewhere in the brain, the scattered nature of these changes in the AIDS brain suggests a local event.

The detection of HIV within MPS cells, MGCs and microglia, but not in neurons or neuroglia throughout the CNS (and optic nerve), suggests that these cells may be involved in the induction of neurological disorders in HIV-infected patients. These cells may act by releasing neurotrophic factors, enzymes or cytokines; by directly releasing virions or envelop glycoprotein; or by releasing inflammatory mediators. For example, HIV-infected macrophages may produce factors such as quinolinic acid, which normally is an agonist for N-methyl-D-aspartate (NMDA) excitatory amino acid receptors, that at high concentrations can be neurotoxic. Elevated CSF levels of quinolinic acid have been found in AIDS patients with neurological complications.

Immunocompetent cells are also known to produce a variety of cytokines that exert regulatory effects on normal immunological and inflammatory processes. Cytokines may regulate production of each other, modulate cell surface cytokine receptors and have antagonistic or synergistic effects on normal cell function. HIV-infected MPS cells and microglia have been reported to release several cytokines, in particular tumor necrosis factor-alpha (TNF), interleukin-1 (IL-1) and interleukin-6 (IL-6). Additionally, HIV-1 infection of promonocytic cells has been shown to prime or sensitize these cells to produce high levels of cytokines upon subsequent antigenic challenge; mononuclear cells from AIDS patients also produce higher levels of TNF MRNA than controls. These cytokines may induce release of cell metabolites, producing toxic effects within the CNS and are reported to enhance HIV-production within MPS cells. Cytokines and other factors (such as quinolinic acid) are thus major candidates as possible mediators of neural tissue damage observed in the AIDS-infected CNS, and the subsequent impairment of normal neural function.

One of the most extensively studied cytokines, TNF, is produced mainly by activated macrophages. TNF is reported to be involved in many processes including cachexia, induction of fever, stimulation of angiogenesis, activation of macrophages, and stimulation of HIV-1 replication in MPS cells. Cytokines, and TNF in particular, have been implicated in a variety of conditions including chronic skin changes seen in psoriasis and hairy cell leukemia.

In vitro, TNF has been shown to induce pathological changes in myelinated fibers and oligodendrocytes, and to induce astroglial proliferation. Astroglial proliferation is a common pathological feature of the HIV-infected CNS. Both microglia and astrocytes have been induced to produce TNF. Studies of chronic progressive multiple sclerosis (MS) patients have found significantly increased levels of CSF TNF. Elevated serum and CSF levels of TNF, IL-1, IL-6 and interferon have also been found in MS patients. Immunohistochemical studies of MS brain tissue have found anti-TNF labelling localized to fibrous astrocytes and macrophages. TNF is, therefore, clearly implicated as being directly involved in axon demyelination, or indirectly involved by activating this process via a cell-mediated pathway.

While some studies have found no increase in CSF TNF levels in patients displaying various complications of AIDS (although increased levels of the cytokines IL-1B and IL-6 were noted in about 50% of patients) , other studies have identified the presence of elevated serum TNF levels in AIDS patients, patients with AIDS-related complex (ARC), and children with AIDS encephalopathy. AIDS patients with CNS involvement (albeit some had secondary infectious diseases) have been reported to have elevated serum and CSF TNF levels (CSF>serum). Differing results in various studies of CSF and serum TNF levels in AIDS patients may be due to breakdown of TNF prior to analysis; assay and sample collection techniques, or patient selection. Additionally, serum and CSF levels do not indicate the presence of receptor-bound TNF.

In measurements of CSF TNF levels in AIDS patients described herein, elevated TNF levels have been found on AIDS patients having AIDS dementia (as compared to AIDS patients with no neurological symptoms). In contrast, Grimaldi et al., in Ann. Neurol. 29:21–25 (1991) report no correlation between elevated TNF levels and clinical dementia or CNS demyelination in HIV-infected and AIDS patients.

Accordingly, the studies described herein indicate that there is a relationship between neurological dysfunction and elevated CSF TNF levels. In view of this correlation, the present invention provides a method for the treatment of a subject displaying optic neuropathy associated with acquired immunodeficiency syndrome (AIDS). The invention method comprises orally administering to the subject an amount of pentoxifylline effective to prevent or reduce the expression of tumor necrosis factor (TNF), or neutralize TNF in the central nervous system.

Those of skill in the art can readily determine amounts of pentoxifylline suitable for the above-stated purpose. Typically, an amount in the range of about 200 mg–1 g per dose of pentoxifylline is employed, administered to the subject at least two times a day, with up to four or more doses a day being acceptable. Generally, a dose of about 400 mg is administered to the subject four times a day.

In accordance with another embodiment of the present invention, there is provided a rabbit eye model which is useful for study of the effects of chronic exposure of the optic nerve to TNF and other cytokines.

In accordance with yet another embodiment of the present invention, there is provided a method for the treatment of a subject displaying optic neuropathy associated with acquired immunodeficiency syndrome (AIDS), said method comprising preventing or reducing the expression of tumor necrosis factor (TNF), or neutralizing TNF in the central nervous system.

As employed herein, the phrase "optic neuropathy associated with acquired immunodeficiency syndrome" refers to AIDS associated loss of visual acuity, visual field, color vision and contrast sensitivity in the absence of retinitis.

As employed herein, the phrase "preventing or reducing the expression of tumor necrosis factor (TNF), or neutralizing TNF in the central nervous system" refers to the administration to the subject of agents which block expression of TNF, or which bind TNF which has been expressed (thereby inactivating the TNF). Administration of such agents can be accomplished in a variety of ways, e.g., orally, intravenously, intrathecally, parenterally, intramuscularly, intraperitoneally, subcutaneously, transdermally, employing controlled release delivery systems (such as, for example, by slow release from polymeric matrices having a controlled pore size; by slow release with polymers which decompose at a controlled rate, etc.), and the like.

As employed herein, the phrase "TNF blocker" refers to agents which are capable of preventing or reducing the expression of tumor necrosis factor (TNF), or neutralizing TNF (if already expressed). The term includes anti-TNF antibodies and antisense DNA capable of blocking expression of TNF.

Examples of TNF blockers contemplated for use in the practice of the present invention, in addition to anti-TNF antibodies and antisense DNA capable of blocking expression of TNF, include pentoxifylline (1-(5-oxohexyl)-3,7-dimethyl xanthine), theobromine, isobutyl methylxanthine, theophylline, dibutyryl cAMP, and the like.

In accordance with still another embodiment of the present invention, there is provided a method for the treatment of a subject displaying central nervous system (CNS) impairment associated with acquired immunodeficiency syndrome (AIDS), said method comprising preventing or reducing the expression of tumor necrosis factor (TNF), or neutralizing TNF in the CNS.

As employed herein, the phrase "central nervous system impairment associated with acquired immunodeficiency syndrome" refers to such ailments as toxoplasmosis, cryptococcal meningitis, cerebrovascular lesion, neoplasms, and the like, which commonly occur in AIDS patients.

In accordance with still another embodiment of the present invention, there is provided a method for the treatment of a subject displaying at least one central nervous system (CNS) impairment, said method comprising preventing or reducing the expression of tumor necrosis factor (TNF), or neutralizing TNF in the CNS.

As employed herein, the phrase "CNS impairment" refers to immune disorder diseases which effect the central nervous system, such as optic neuritis, multiple sclerosis, Devic's disease, and other demyelinative processes.

The invention will now be described in greater detail by reference to the following non-limiting examples.

EXAMPLES

EXAMPLE I

Histopathology and Immunocytochemistry

To describe the histopathological changes in optic nerves from AIDS patients without retinopathy, control and AIDS optic nerves have been examined using light and electron microscopy.

Light microscopy with special staining techniques revealed only very few degenerative profiles in the normal optic nerve, however, extensive diffuse patchy areas of axonal degeneration were visible in AIDS optic nerves. All parts of the retina (posterior pole, mid periphery and far periphery) were equally represented by optic nerve retinotopy.

DNA Polymerase Chain Reaction (PCR) techniques were used to demonstrate HIV DNA in optic nerves from HIV-seropositive cadavers although DNA was detected in only one retinal specimen. In addition, HIV antigens (indicated by labelling for gp41 and p24 antigens) were demonstrated in scattered macrophage-like cells within four of the five optic nerves from HIV-positive cadavers using an avidin-biotin immunoperoxidase technique followed by glucose oxidase staining [Skolnik et al., American Journal of Ophthalmology 107:361-372 (1989)]. Many of these cells co-stained with a monoclonal antibody to Leu-M3, a macrophage marker.

Ultrastructural studies revealed a number of features:

Various stages of axonal degeneration were observed; axons that had just begun degenerating were adjacent to mature degenerated profiles, some of which had been reensheathed by oligodendrocytes. Normal axons were also visible interspersed among the degenerating axons. Axonal degeneration was not confined to specific regions of the optic nerve.

Clusters of oligodendrocytes with electron lucent cytoplasm, myelin inclusions and viral-like structures were observed. In some areas necrotic cells (presumptive oligodendrocytes) with pyknotic nuclei, vacuolated cytoplasm, retracted processes and disrupted mitochondria were visible.

Reactive astrocytes were observed both within and between fascicles, characterized by dense cytoplasmic intermediate filaments, irregular and enlarged nuclei and hypertrophic processes. Lysosomes and cytoplasmic inclusions of cellular debris, probably myelin remnants and debris from degenerating oligodendrocytes, were often observed within astrocytes.

Active mononuclear phagocyte series (MPS) cells with ruffled plasma membranes, dense cytoplasm and lysosomes were visible in AIDS optic nerves, as well as in vessel lumens.

AIDS optic nerves also displayed thickened septa, with increased numbers of fibroblasts, many of which appeared to be activated.

EXAMPLE II

Morphometry

The PPD staining technique described by Sadun and Schaechter, supra has been applied to identify both degenerated profiles and intact axons in conjunction with a computerized image enhancement/analysis system. Quantitative analysis of degeneration and total optic nerve fiber counts were measured in patients with AIDS (without secondary retinal infections) and age-matched controls.

Morphometric analyses of eight optic nerves from eight AIDS patients and four normal age-matched controls are described in a recently published paper [Tenhula et al., Am. J. Ophthalmol. 113:14-20 (1992)]. The results are summarized in Table I.

TABLE 1

| Data Summary | | | | |
|---|---|---|---|---|
| | Control Data (n = 4) | AIDS Data (n = 8) | Unpaired t-test | p-value |
| Total Axon Population | 1,507,117 ± 443,123 | 880,073 ± 199,616 | −3.48 | 0.006 |
| Axon Density (axons/1000 μm$^2$) | 252.0 ± 27.8 | 179.3 ± 30.4 | −4.00 | 0.003 |

TABLE 1-continued

Data Summary

| | Control Data (n = 4) | AIDS Data (n = 8) | Unpaired t-test | p-value |
|---|---|---|---|---|
| Degeneration (profiles/100 intact axons) | 1.0 ± 0.6 | 6.6 ± 2.3 | −4.67 | 0.001 |
| Axonal Diameter (μm) | 0.86 ± 0.1 | 0.92 ± 0.1 | 1.17 | 0.269 |

The data in the Table indicate that the mean intact axon population and the mean axon density values were significantly reduced in AIDS optic nerves, compared to the control optic nerves (p=0.006 and p=0.003 respectively: unpaired t-test). The mean intact axon population in the AIDS optic nerves was 880,073±199,616, compared to 1,507,117±443,123 for the controls.

In the normal optic nerves there were few or no degenerated profiles. The eight AIDS optic nerves all showed varying degrees of axonal degeneration. There were significantly more degenerated profiles in AIDS optic nerves than in control optic nerves (p=0.001, unpaired t-test).

There was no significant difference between the mean diameters of axons in AIDS versus normal optic nerves.

The nerve fiber spectrum from optic nerves with early or late injury from AIDS does not reflect the selective involvement of one class of axons as distinguished by size.

There appeared to be a ubiquitous loss of axons of all calibers.

The distribution of degeneration did not appear to reflect regional involvement of the retina. In cases of retinal nerve fiber layer infarcts, one would expect to see isolated clusters of degeneration in the optic nerve, corresponding to specific nerve fiber layer bundles. This was infrequently seen in AIDS optic nerves. Additionally, zones of regional infarction in the retina were not common. Remarkably, small isolated degenerated profiles were found in equal densities in the middle, mid-peripheral and peripheral areas of the optic nerve. This indicated that this sparse degeneration was not a manifestation of a theoretical subclinical, tiny nerve fiber layer infarcts found only in the peripheral retina.

EXAMPLE III

Psychophysics

To study the function of the central visual pathway (macula and optic nerve) distance Snellen visual acuity, contrast sensitivity (measured by sine wave gratings) and color vision (measured with the Farnsworth-Munsell (FM) 100 Hue Test) were tested in AIDS patients without retinitis, as reported recently [Quiceno et al., supra].

Eighty male subjects between the ages 25 and 49 years were selected and classified in one of four groups:

(a) normal control patients (n=18), (b) asymptomatic HIV-positive patients (n=19);

(c) AIDS-related complex patients (n=20), and (d) AIDS patients (N=21).

Only subjects without history of organic eye disease, congenital or acquired color vision defect, and best corrected distance Snellen visual acuity of 20/20 or better were included. The following observations were made:

a) Contrast sensitivity studies found a significant deficit in contrast threshold in AIDS patients at four of five spatial frequencies and in AIDS-related complex patients at three of five spatial frequencies examined.

b) There was no significant difference in the times of performance for the FM 100 Hue Test among the study groups. However, the age-corrected square root error score of AIDS patients were significantly higher than those of either AIDS-related complex, HIV positive or HIV negative patients (p<0.001; Duncan's multiple range test).

These results suggest that in the AIDS retina, the P cell system (reported as being involved in color perception and contrast sensitivity, see Quiceno et al., supra) may be preferentially affected.

EXAMPLE IV

TNF levels in CSF of AIDS Patients

Using a commercially available ELISA immunoassay, TNF levels in CSF from 10 AIDS patients with no neurological symptoms and AIDS encephalopathy have been measured. TNF concentration in AIDS encephalopathy patients ranged from 515–701 pg/ml. Another 10 AIDS patients without encephalopathy were also studied. Their CSF had TNF levels ranging from 4–12 pg/ml. These results are consistent with the hypothesis that TNF may be involved in mediating neural damage in the CNS (and optic nerve).

EXAMPLE V

Rabbit Eye Model

Optic nerves have been examined from ten rabbits which had TNF in Hank's solution injected into the vitreous chamber, just anterior to the optic disc [as described by Madigan, M. C., Dugel, P. U., Rao, N. S., Tenhula, W. N., Gill, P. S., and Sadun, A. A. in "Time and dose dependent axonal loss in rabbit optic nerves following exposure to tumor necrosis factor-alpha" submitted to Current Eye Research (1992)] of one eye only, the other eye serving as a control. To control for the effect of injecting Hank's solution, another five rabbits were injected with Hank's solution sans TNF. optic nerves from both eyes were examined at one week, 4, 8, 12 and 24 weeks (TNF concentrations: $10^4$ and $10^2$ Units/ml respectively) following TNF injection.

EXAMPLE VI

Light and Electron Microscopy

Light microscopy of PPD stained sections revealed few or no degenerating profiles in the control rabbit optic nerves. There was little difference between control and TNF exposed optic nerves one week after injection, however, after 4 weeks, areas of degeneration were clearly visible for both concentrations of TNF. Eight weeks after TNF injection, marked axonal degeneration was still visible in areas of the optic nerves; however, at the 12 and 24 week interval there appeared to be fewer, but possibly larger, degenerating profiles. Axonal degeneration was interspersed between normal axons.

Ultrastructural studies of these nerves revealed a number of features:

Axonal degeneration was observed to consistently occur after short survivals. Various stages of axonal degeneration were observed over time in nerves exposed to both TNF concentrations.

A number of denuded processes consistent with unmyelinated axons were observed, particularly at 12 and 24 weeks after TNF injection.

Reactive astrocytes with hypertrophied processes, dense cytoplasmic intermediate filaments, many mitochondria and cytoplasmic lysosomal granules were obvious in TNF-exposed optic nerves. These reactive astrocytes were particularly obvious at 8, 12 and 24 weeks after TNF injection.

MPS cells appeared to be activated in optic nerves following TNF injection. These cells displayed ruffled plasma membranes, increased ribosomes and rough endoplasmic reticulum and in some instances lysosomes.

Increased proportions of large axons were observed at 8 and 12 weeks after TNF injection, with fewer after 24 weeks.

Rabbits, unlike humans, have a myelinated bundle of nerve fibers in their retina, thus allowing for PPD staining of axonal degeneration at the level of the retina. The retinas of two rabbits have also been examined 6 months after intravitreal injection of 10 and 106 units/ml TNF respectively. The myelinated areas of the control rabbit retina appeared normal, with no obvious degeneration. TNF-injected eyes displayed non-specific degeneration in the myelinated region of the retina, similar to that observed in the optic nerve following TNF injection. At higher magnification, recently degenerated profiles were observed in the retina; greater numbers of profiles were visible in the retina exposed to 106 units/ml TNF compared to the retina exposed to 10 units/ml TNF. Macrophages, some associated with axonal degeneration, were also visible in the inner layers of the rabbit retina.

EXAMPLE VII

Morphometric Analysis

Figure 2:
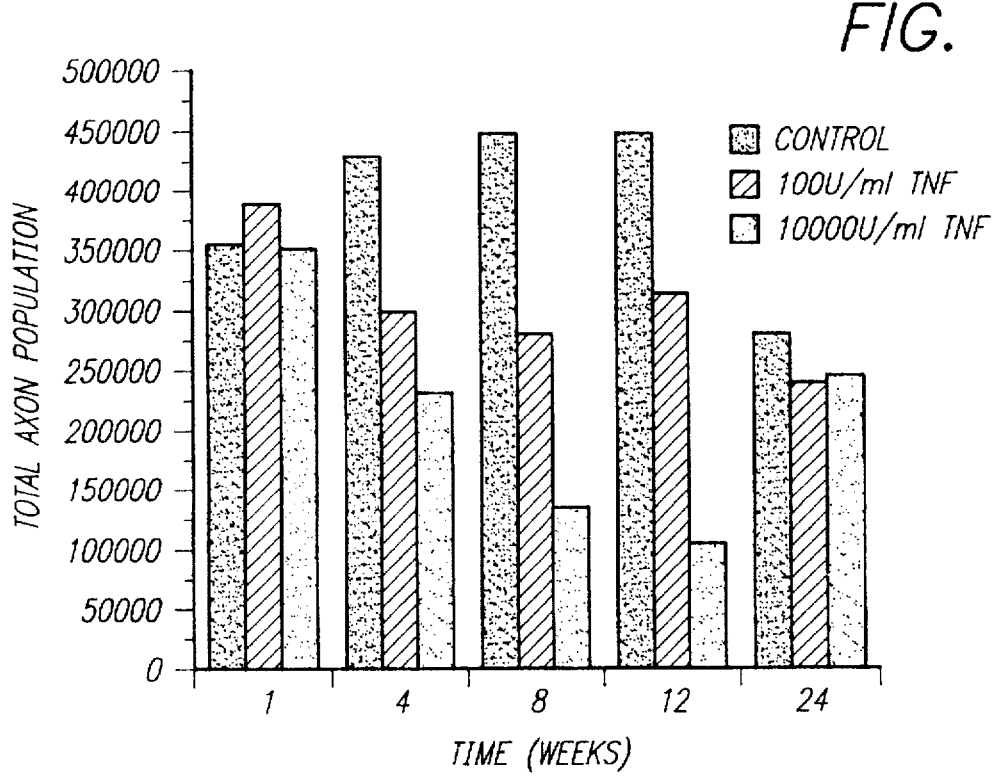
FIG. 2 shows the effect of TNF treatment on rabbit optic nerve axon population as a function of time.

PPD stained cross-sections of optic nerves were examined using a semi-automated image analysis system; morphometric analysis of both intact axons and degenerated profiles was conducted. Sixteen sectors from a cross-section of each nerve were studied. The density of axons was then used to calculate the total number of intact axons per optic nerve. The following observations have been made:

a) Overall there was a significant decrease in total intact axon population when optic nerves exposed to $10^4$ and $10^2$ Units/ml TNF, respectively, were compared to control optic nerves (10 Units/ml TNF vs control: t=2.617, p=0.059 and 10 Units/ml TNF vs control: t=2.331, p=0.08; paired t-test, FIG. 1). The total intact axon population was also significantly less in optic nerves exposed to higher concentrations of TNF (10 Units/ml TNF vs 102 Units/ml TNF: t=2.447, p=0.07; paired t-test).

b) Total axon population decreased with time following TNF injection compared to control optic nerves. This decrease appeared to be dose-dependent with the greater effect observed in the nerves exposed to the higher concentration of TNF (10 Units/ml TNF) (FIG. 2).

c) Twenty four weeks after TNF injection the total axon population increased in the nerve exposed to 10 Units/ml TNF; stabilized in the nerve exposed to 102 nits/ml TNF and decreased in the control optic nerve (FIG. 2).

The pattern of axonal degeneration observed in optic nerves from AIDS patients and from rabbits injected intravitreally with TNF can be explained as follows. In both instances, a diffuse scattered degeneration was observed with normal axons interspersed among degenerating axons. Activated astrocytes and MPS cells were observed in nerves from both human and rabbit; these cell types can be induced to produce TNF (and other cytokines) when activated. TNF is known to be active at very low concentrations, and to have a very short half-life. TNF may also be expressed on the surface of MPS cells and lymphocytes, and may thus act by cell-to-cell contact or by humoral mechanisms. Additionally, a variety of cell types, particularly MPS cells, are known to have TNF receptors via which TNF may be internalized and degraded after binding. Given the above observations, it is suggested that in the optic nerve, TNF action is a local event affecting only a few axons and oligodendrocytes before its effect is diminished (either by binding to receptors or proteins or by a loss of activity due to its short half-life). The various stages of axonal degeneration observed may also reflect the effects of transient increases in local TNF over time (TNF either expressed on cell surfaces or released from activated MPS cells or astrocytes) accompanied by activation of a cytokine cascade.

While the invention has been described in detail with reference to certain preferred embodiments thereof, it will be understood that modifications and variations are within the spirit and scope of that which is described and claimed.

That which is claimed is:

1. A method for treating neuronal degeneration in a subject displaying optic neuropathy associated with acquired immunodeficiency syndrome (AIDS), said method comprising orally administering to said subject an amount of pentoxifylline effective to prevent or reduce the expression of tumor necrosis factor (TNF), or neutralize TNF in the central nervous system.

2. A method according to claim 1 wherein said effective amount comprises in the range of about 200 mg up to 1 g per dose of pentoxifylline, administered to said subject at least two, and up to four times per day.

3. A method for treating neuronal degeneration in a subject displaying optic neuropathy associated with acquired immunodeficiency syndrome (AIDS), said method comprising administering to said subject an amount of an agent effective for preventing or reducing the expression of tumor necrosis factor (TNF), or neutralizing TNF in the central nervous system.

4. A method according to claim 3 wherein the agent is a TNF blocker.

5. A method for the treatment of a subject displaying optic neuropathy associated with acquired immunodeficiency syndrome (AIDS), said method comprising preventing or reducing the expression of tumor necrosis factor (TNF), or neutralizing TNF in the central nervous system by administration of an effective amount of pentoxifylline.

6. A method according to claim 5 wherein said pentoxifylline is orally administered to said subject.

7. A method according to claim 6 wherein said effective amount comprises in the range of about 200 mg up to 1 g per dose of pentoxifylline, administered to said subject at least two, and up to four times per day.

8. A method for treating neuronal degeneration in a subject displaying a central nervous system (CNS) impairment associated with acquired immunodeficiency syndrome (AIDS), said method comprising administering to said subject an amount of an agent effective for effective to preventing or reducing the expression of tumor necrosis factor (TNF), or neutralizing TNF in the CNS.

9. A method according to claim 8 wherein the agent is a TNF blocker.

10. A method for the treatment of a subject displaying central nervous system (CNS) impairment associated with acquired immunodeficiency syndrome (AIDS), said method comprising preventing or reducing the expression of tumor necrosis factor (TNF), or neutralizing TNF in the CNS by administration of an effective amount of pentoxifylline, theobromine, isobutyl methylxanthine, theophylline, or dibutyryl cAMP.

11. A method according to claim 10 wherein said TNF blocker is pentoxifylline.

12. A method according to claim 9 wherein said TNF blocker is administered to said subject orally, intravenously, intrathecally, parenterally, intramuscularly, intraperitoneally, subcutaneously, transdermally, or employing controlled release delivery systems.

13. A method according to claim 11 wherein said TNF blocker is orally administered to said subject.

14. A method according to claim 9 wherein said CNS impairment associated with AIDS is optic neuropathy.

15. A method according to claim 14 wherein said optic neuropathy is AIDS associated retinopathy.

16. A method for treating neuronal degeneration in a subject displaying optic neuropathy associated with at least one demyelinating central nervous system (CNS) disease, said method comprising administering to said subject an amount of an agent effective for preventing or reducing the expression of tumor necrosis factor (TNF), or neutralizing the expression of TNF in the CNS.

17. A method according to claim 16, wherein said disease is optic neuritis.

18. A method according to claim 16, wherein said disease is Devic's disease.

* * * * *